United States Patent
Matsunaga et al.

(10) Patent No.: US 12,196,622 B2
(45) Date of Patent: Jan. 14, 2025

(54) TEMPERATURE MEASUREMENT DEVICE AND TEMPERATURE MEASUREMENT METHOD

(71) Applicant: Nippon Telegraph and Telephone Corporation, Tokyo (JP)

(72) Inventors: Daichi Matsunaga, Tokyo (JP); Yujiro Tanaka, Tokyo (JP); Michiko Seyama, Tokyo (JP)

(73) Assignee: Nippon Telegraph and Telephone Corporation, Tokyo (JP)

(*) Notice: Subject to any disclaimer, the term of this patent is extended or adjusted under 35 U.S.C. 154(b) by 603 days.

(21) Appl. No.: 17/437,246

(22) PCT Filed: Apr. 3, 2020

(86) PCT No.: PCT/JP2020/015363
§ 371 (c)(1),
(2) Date: Sep. 8, 2021

(87) PCT Pub. No.: WO2020/213437
PCT Pub. Date: Oct. 22, 2020

(65) Prior Publication Data
US 2022/0170800 A1    Jun. 2, 2022

(30) Foreign Application Priority Data
Apr. 19, 2019 (JP) .................. 2019-079832

(51) Int. Cl.
*G01K 13/20*    (2021.01)
*G01K 1/16*    (2006.01)

(52) U.S. Cl.
CPC .............. *G01K 13/20* (2021.01); *G01K 1/16* (2013.01)

(58) Field of Classification Search
None
See application file for complete search history.

(56) References Cited

U.S. PATENT DOCUMENTS

| | | | |
|---|---|---|---|
| 2009/0306536 A1* | 12/2009 | Ranganathan | A61B 5/01 600/549 |
| 2015/0055681 A1* | 2/2015 | Tsuchida | G01K 13/20 374/183 |
| 2015/0126834 A1* | 5/2015 | Wang | B32B 38/10 156/247 |
| 2017/0003175 A1 | 1/2017 | Sakaguchi et al. | |

FOREIGN PATENT DOCUMENTS

| | | |
|---|---|---|
| JP | 2014182073 A | 9/2014 |
| JP | 2015152502 A | 8/2015 |
| WO | 2012042759 A1 | 4/2012 |

OTHER PUBLICATIONS

Feng, et al., "Development of an improved wearable device for core body temperature monitoring based on the dual heat flux principle," institute of Physics and Engineering in Medicine, vol. 38, No. 4, Mar. 17, 2017, pp. 652-668.

* cited by examiner

*Primary Examiner* — Erica S Lin
(74) *Attorney, Agent, or Firm* — Slater Matsil, LLP

(57) ABSTRACT

A temperature measurement device includes a first probe that measures a physical quantity related to a temperature of a substance on the basis of a first reference, a second probe that measures a physical quantity related to a temperature of the substance on the basis of a second reference different from the first reference, and a heat conductive member that covers the first probe and the second probe and transports heat from the substance.

14 Claims, 10 Drawing Sheets

TEMPERATURE MEASUREMENT DEVICE AND TEMPERATURE MEASUREMENT METHOD

CROSS-REFERENCE TO RELATED APPLICATIONS

This application is a national phase entry of PCT Application No. PCT/JP2020/015363, filed on Apr. 3, 2020, which claims priority to Japanese Application No. 2019-079832, filed on Apr. 19, 2019, which applications are hereby incorporated herein by reference.

TECHNICAL FIELD

The present disclosure relates to a temperature measurement device and a temperature measurement method for measuring a temperature of a deep area of a substance, particularly a core body temperature of a living body.

BACKGROUND

In a substance such as a living body, for example, when a certain depth is exceeded from the epidermis toward a deep area, there is a temperature region that is not affected by changes in outside air temperature and the like, and the temperature of that portion is referred to as a core body temperature or a core temperature. On the other hand, a temperature of a surface layer of the living body that is susceptible to changes in the outside air temperature is referred to as a body surface temperature. The body surface temperature has been measured by a percutaneous thermometer. The body temperature measured by such a known percutaneous thermometer may not reflect the core body temperature. Therefore, it is difficult to directly measure the core body temperature, which is the temperature of a deep area of the living body, in the same way as the body surface temperature.

Here, techniques have been proposed in which the core body temperature is estimated by assuming a thermal equivalent circuit in which the process of heat transfer in the living body is substitute with an electric circuit and then using the body surface temperature measured by a temperature sensor (refer to Non Patent Literature 1).

FIG. 14 is a block diagram of a temperature measurement device that estimates the core body temperature of a living body by a dual heat flux method in the related art. Two probes 310, 320 are disposed on a surface of a living body 300. The probes 310, 320 provided in a living body internal temperature measurement device in the related art each include a heat insulating member having thermal resistances different from each other (thermal resistances $R_1$, $R_2$). The probe 310 measures body surface temperatures $T_1$, $T_3$ via the heat insulating member ($R_1$). The probe 320 measures body surface temperatures $T_2$, $T_4$ via the heat insulating member ($R_2$).

Heat fluxes $H_1$, $H_2$ of the respective probes 310, 320 are determined by the following equations (1):

$$H_1 = (T_1 - T_3)/R_1 \quad (1)$$
$$H_2 = (T_2 - T_4)/R_2$$

A core body temperature $T_B$ is expressed by equations (2) below. Here, R indicates a thermal resistance of the living body, which is an unknown value.

$$T_B = T_1 + R \cdot H_1 \quad (2)$$
$$T_B = T_2 + R \cdot H_2$$

When the above equations (2) are rewritten, the core body temperature $T_B$ is expressed by the following equation (3).

Math. 1

$$T_B = \frac{T_2 \cdot H_1 - T_1 \cdot H_2}{H_1 - H_2} \quad (3)$$

By using the above equation (3), it is possible to estimate the core body temperature $T_B$. However, the living body 300 is actually constituted by continuous tissue, and a leakage $H_L$ of a heat flux occurs because of bonding with adjacent tissue. This leakage $H_L$ of the heat flux occurs in the living body interior and therefore cannot be measured. Here, Non Patent Literature 1 discloses a technique for correcting an estimation of the core body temperature $T_B$ to estimate the core body temperature $T_B$ more accurately.

As illustrated in FIG. 15, the probes 310, 320 having thermal resistances different from each other are disposed on the surface of the living body 300, and the core body temperature $T_B$, which takes into account leakages $H_{L3}$, $H_{L2}$ of the heat fluxes, is expressed by the following equations (4).

$$T_B = T_1 + R \cdot (H_1 + H_{L1}) \quad (4)$$
$$T_B = T_2 + R \cdot (H_2 + H_{L2})$$

The core body temperature $T_B$ can be expressed by equation (5) using a ratio K of the leakage of the heat fluxes of the two sensors (probes 310, 320).

Math. 2

$$T_B = \frac{K \cdot T_2 \cdot H_1 - T_1 \cdot H_2}{K \cdot H_1 - H_2} \quad (5)$$

Here, the ratio K of the leakage of the heat fluxes of the two probes 310, 320 is expressed by equation (6).

Math. 3

$$K = \frac{(H_1 + H_{L1})/H_1}{(H_2 + H_{L2})/H_2} \quad (6)$$

The ratio K of the leakage of the heat fluxes of the above equations (5), (6) is calibrated by an initial input $T_{B(0)}$ of the core body temperature $T_B$, as expressed by the following equation (7).

Math. 4

$$K_{(0)} = \frac{(T_{B(0)} - T_{1(0)})/H_{1(0)}}{(T_{B(0)} - T_{2(0)})/H_{2(0)}} \quad (7)$$

CITATION LIST

Non Patent Literature

Non Patent Literature 1: J. Feng, C. Zhou, C. He, Y. Li, X. Ye, "Development of an improved wearable device for core body temperature monitoring based on the dual heat flux principle," Med. Eng. Phys., Vol. 38, No. 4, 652-668, April 2017.

SUMMARY

Technical Problem

However, in the technique in the related art, the value of the ratio K of the leakage of the heat fluxes changes according to a change in the thermal resistances between the probes 310, 320 and the outside air, and thus there is a problem in that an error occurs in the estimated value of the core body temperature $T_B$.

In order to solve the problem described above, an object of the present disclosure is to provide a temperature measurement technique capable of more accurately estimating a temperature of a deep area of a substance regardless of a change in thermal resistance to outside air.

Means for Solving the Problem

To solve the problems described above, a temperature measurement device according to the present disclosure includes a first probe configured to measure a physical quantity related to a temperature of a substance based on a first reference, a second probe configured to measure a physical quantity related to a temperature of the substance based on a second reference different from the first reference, and a heat conductive member configured to cover the first probe and the second probe and transport heat from the substance.

Further, in the temperature measurement device according to the present disclosure, the first probe may come into contact with a surface of a living body to measure a physical quantity related to a temperature of the living body, the second probe may have a thermal resistance different from a thermal resistance of the first probe and come into contact with the surface of the living body to measure a physical quantity related to a temperature of the living body, and the heat conductive member may transport heat transferred from the surface of the living body.

Further, in the temperature measurement device according to the present disclosure, the heat conductive member may comprise a material having a thermal conductivity higher than a thermal conductivity of outside air.

Further, in the temperature measurement device according to the present disclosure, the heat conductive member may include a metal material.

Further, in the temperature measurement device according to the present disclosure, the heat conductive member may include aluminum or copper.

Further, in the temperature measurement device according to the present disclosure, the heat conductive member may include graphene.

Further, in the temperature measurement device according to the present disclosure, the first probe may include a first thermal resistor, a first temperature measurement unit provided to the first thermal resistor and configured to measure a temperature of the substance, and a first heat flux measurement unit provided to the first thermal resistor and configured to measure a heat flux, and the second probe may include a second thermal resistor having a thermal resistance different from a thermal resistance of the first thermal resistor, a second temperature measurement unit provided to the second thermal resistor and configured to measure a temperature of the substance, and a second heat flux measurement unit provided to the second thermal resistor and configured to measure a heat flux.

Further, to solve the problems described above, a temperature measurement method according to the present disclosure is a temperature measurement method executed using the temperature measurement device described above, the temperature measurement method including calculating, using a first bridge circuit including a thermal resistance of a substance and a thermal resistance of a first probe, a first temperature of the substance measured by the first probe, calculating, using a second bridge circuit including the thermal resistance of the substance and a thermal resistance of a second probe, a second temperature of the substance measured by the second probe, and estimating a temperature of a deep area of the substance based on the first temperature that is calculated and the second temperature that is calculated.

Effects of Embodiments of the Invention

According to the present disclosure, the first probe and the second probe are each covered with a heat conductive member that transports heat from a substance, making it possible to more accurately estimate a temperature of a deep area regardless of a change in thermal resistance to outside air.

DETAILED DESCRIPTION OF ILLUSTRATIVE EMBODIMENTS

Preferred embodiments of the present disclosure will be described in detail below with reference to FIGS. 1 to 13.

Summary of Embodiments of the Invention

First, a temperature measurement device according to the present disclosure includes a first probe that measures a physical quantity related to a temperature of a substance on the basis of a first reference, a second probe that measures a physical quantity related to a temperature of the substance on the basis of a second reference, and a heat conductive member that covers the first probe and the second probe and transports heat from the substance. Hereinafter, the temperature measurement device will be described by applying the device to a living body internal temperature measurement device 100 that measures a temperature in a living body.

First, an overview of the living body internal temperature measurement device 100 according to an embodiment of the present disclosure will be described with reference to FIGS. 1 to 5.

Figure 1:
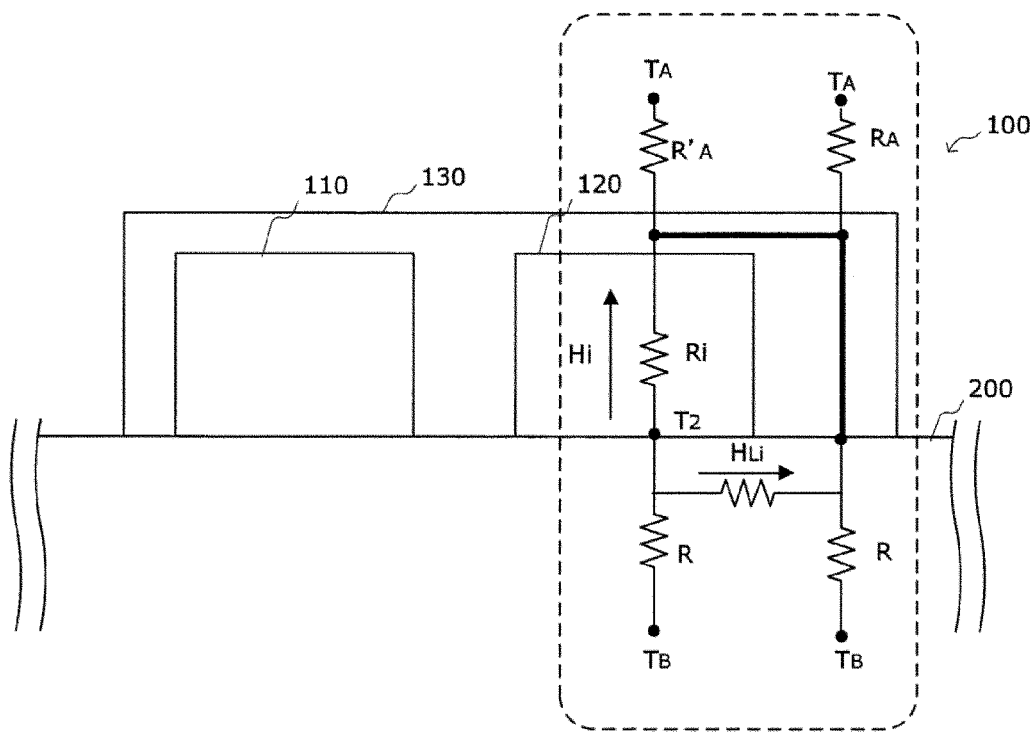
FIG. 1 is a diagram for explaining an overview of a living body internal temperature measurement device according to an embodiment of the present disclosure.

FIG. 1 illustrates a block diagram of the living body internal temperature measurement device 100 according to this embodiment and a thermal equivalent circuit thereof. As illustrated in FIG. 1, in the living body internal temperature measurement device 100 according to the embodiment, two probes (first probe and second probe) 110, 120 are disposed in contact with an epidermis of a living body 200. Further, a heat conductive member 130 is provided covering an outer peripheral surface where the two probes 110, 120 are not in contact with the epidermis.

The probes 110, 120 have thermal resistances (first reference, second reference) that differ from each other, and each measures a body temperature and a heat flux in the epidermis of the living body 200. Note that details of a configuration in which the probes 110, 120 are provided will be described later.

The heat conductive member 130 is made of a material having a thermal conductivity higher than that of outside air and, for example, a metal material such as aluminum or copper or graphene can be used. The heat conductive member 130 transports heat transferred from the surface of the living body 200, equalizing a temperature of the peripheries of the probes 110, 120 and the temperature of the surface of the living body 200. The use of a material having a high thermal conductivity as the heat conductive member 130 is one of the characteristics of this embodiment.

In the thermal equivalent circuit including the living body 200, the probe 120, the heat conductive member 130, and the outside air and indicated by the broken line frame in FIG. 1, $T_A$ denotes an outside air temperature, $R_A$ and $R'_A$ denote thermal resistances to the outside air, $R_i$ denotes a thermal resistance of the probe 120 and is a known value, $H_i$ denotes a heat flux of the thermal resistance $R_i$, R denotes a thermal resistance of the living body 200, and $H_{Li}$ denotes a leakage of the heat flux that occurs in an interior of the living body 200.

Figure 2:
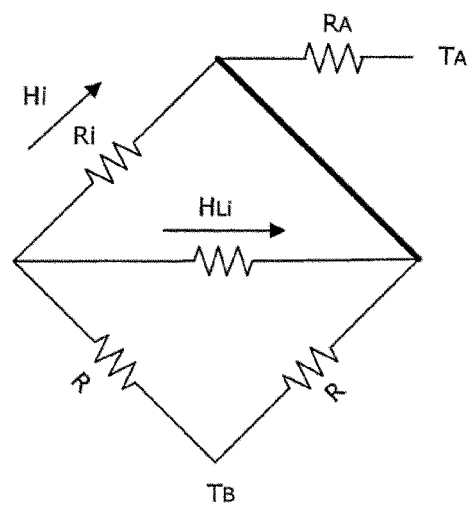
FIG. 2 is a diagram for explaining an overview of the living body internal temperature measurement device according to the embodiment.

The probe 120 illustrated in FIG. 1 and a thermal resistance of the periphery are coupled to form a bridge circuit illustrated in FIG. 2. In the bridge circuit illustrated in FIG. 2, the heat 0130 is provided, and thus the thermal resistance $R_A$ to the outside air is connected to the outside of the bridge circuit. Therefore, even if the thermal resistance $R_A$ to the outside air changes, the ratio K of the leakage of the heat fluxes expressed by equation (6) described above does not change. Note that the bold line of the thermal equivalent circuit in FIG. 1 corresponds to the bold line in the bridge circuit in FIG. 2.

Figure 3:
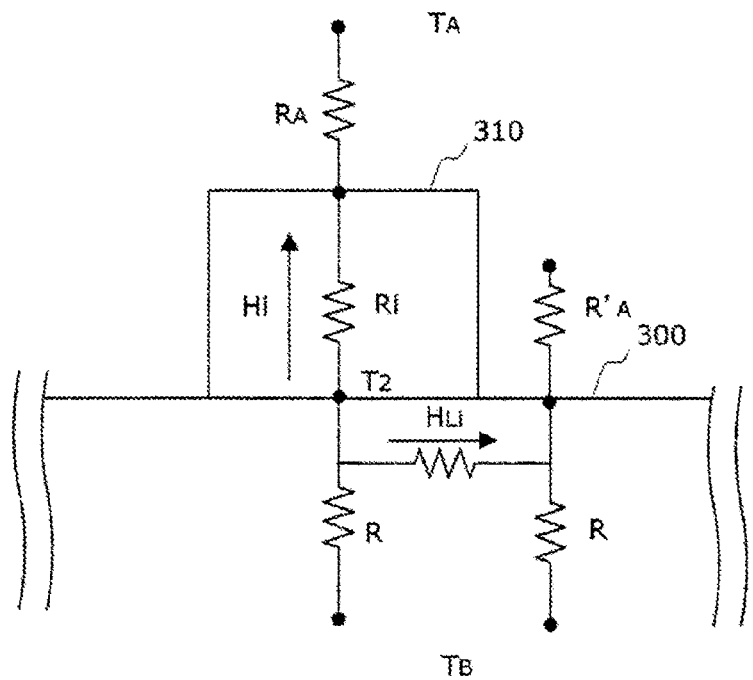
FIG. 3 is a diagram illustrating a related art example for comparison with the living body internal temperature measurement device according to the embodiment.
Figure 4:
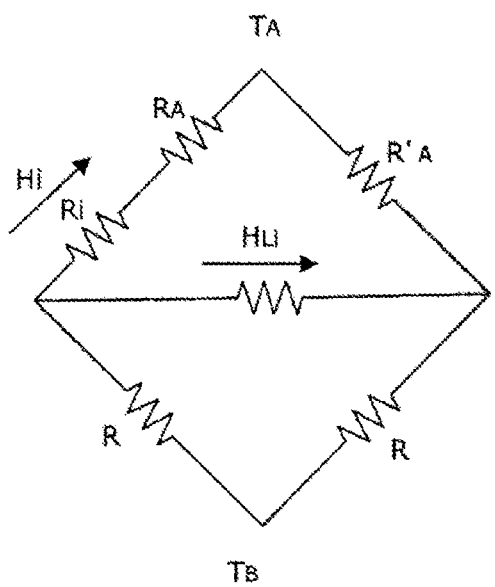
FIG. 4 is a diagram illustrating the related art example for comparison with the living body internal temperature measurement device according to the embodiment.

On the other hand, in the related art example illustrated in FIGS. 3 and 4, which is not provided with the heat conductive member 130, in the bridge circuit in which the probe 310 and the thermal resistance of the periphery are coupled, the thermal resistance $R_A$ to the outside air exists in the bridge circuit. Therefore, the ratio K of the leakage of the heat fluxes expressed by equation (6) described above changes in value by a change in the thermal resistance $R_A$ to the outside air. In this way, in the related art example, when the core body temperature $T_B$ is estimated by equation (5) using the ratio K of the leakage of the heat fluxes, an error may occur in the estimated value.

Here, the thermal resistance $R_A$ to the outside air also depends on a convection state of the outside air. When the convection state of the outside air changes, the thermal resistance $R_A$ to the outside air changes, and an error occurs in the value of the estimated core body temperature $T_B$ as well.

Figure 5:
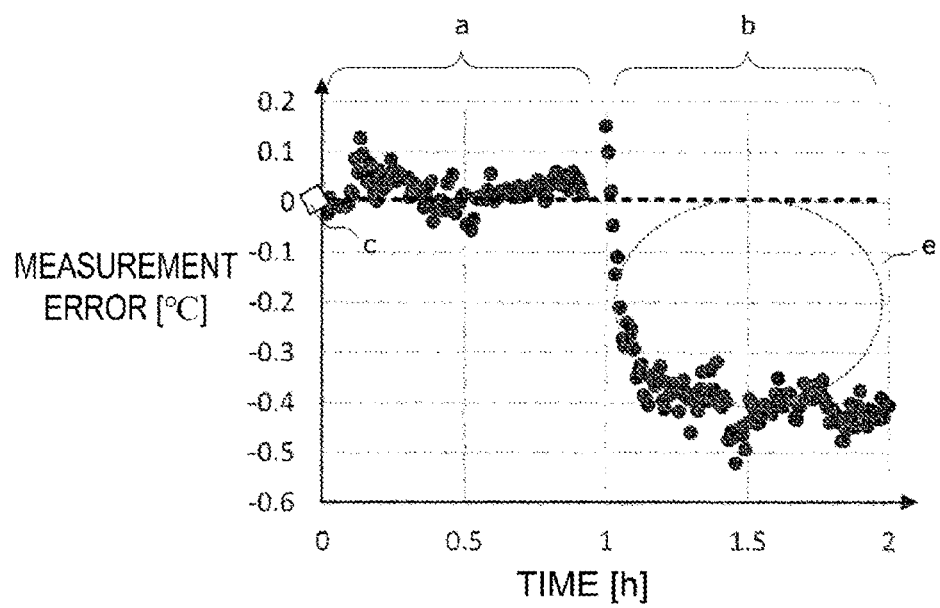
FIG. 5 is a diagram for explaining an overview of the living body internal temperature measurement device according to the embodiment.

FIG. 5 is a graph in which the measurement error of the core body temperature $T_B$ estimated in accordance with a change in the convection state of the outside air is plotted in time series. The horizontal axis represents time and the vertical axis represents measurement error. In FIG. 5, point c denotes a calibration point of equation (7) described above, region a denotes a time zone in which no convection occurs in the outside air, and region b denotes the measurement error in a time zone where there is convection in the outside air. As understood from FIG. 5, the measurement error is larger when convection occurs in the outside air (region e) compared to when there is no convection in the outside air.

As described above, the living body internal temperature measurement device 100 according to this embodiment includes the heat conductive member 130 that covers the periphery of each of the probes 110, 120 that come into contact with the surface of the living body 200 and measure temperature, and thus, even when the convection state of the outside air changes, causing the thermal resistance $R_A$ to change, it is possible to estimate the core body temperature $T_B$ that is not dependent on the thermal resistance $R_A$.

Embodiment

A detailed configuration of the living body internal temperature measurement device 100 according to the embodiment of the present disclosure described above will be described below with reference to FIGS. 6 to 8.

Figure 6:
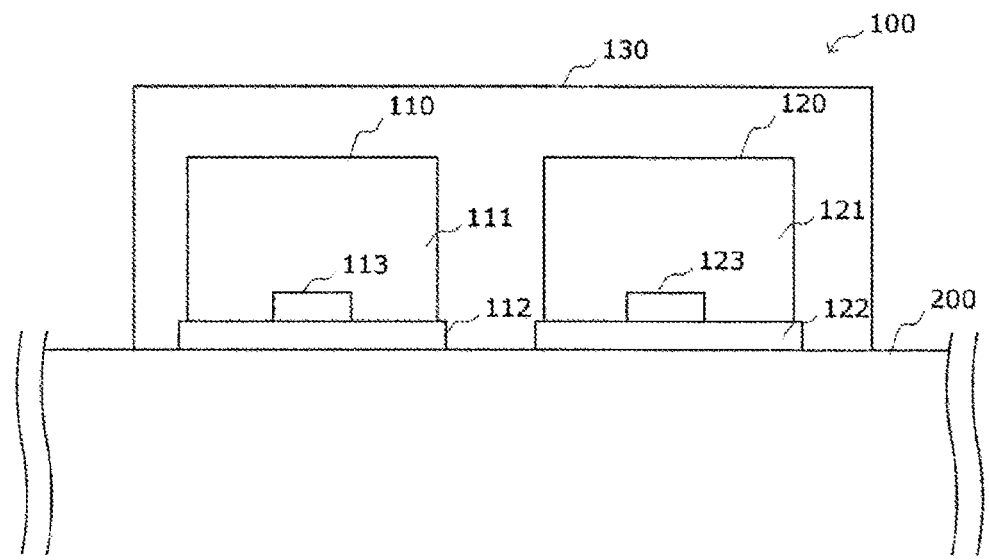
FIG. 6 is a block diagram illustrating a configuration of the living body internal temperature measurement device according to an embodiment of the present disclosure.

As illustrated in FIG. 6, the living body internal temperature measurement device 100 includes the two probes 110, 120 and the heat conductive member 130 formed from aluminum or the like and configured to cover the peripheries of the two probes 110, 120.

The probes 110, 120 respectively include heat insulating members (first thermal resistor, second thermal resistor) 111, 121, heat flux sensors (first heat flux measurement unit, second heat flux measurement unit) 112, 122, and temperature sensors (first temperature measurement unit, second temperature measurement unit) 113, 123.

The heat insulating members 111, 121 constitute thermal resistors and have thermal resistance values that differ from each other. The heat insulating members 111, 121 may have, for example, a same three-dimensional shape formed from materials that differ from each other. Alternatively, the heat insulating members 111, 121 may be configured to have thermal resistance values that differ from each other by heat insulating materials of different thicknesses and materials.

The heat flux sensors 112, 122 are devices that measure a movement of heat per unit time and per unit area. The heat flux sensors 112, 122 are provided at end portions of the heat insulating members 111, 121 on the epidermis side of the living body 200.

The temperature sensors 113, 123 measure the temperature of the surface of the living body 200. Note that the temperature sensors 113, 123 may be constituted by a thermistor, a thermocouple, a temperature measurement resistor, or the like.

As illustrated in FIG. 6, outer peripheral surfaces of each of the probes 110, 120 are covered by the heat conductive member 130 formed from a material having a high thermal conductivity, such as a metal such as aluminum or copper or a graphene sheet, and the outside air does not come into direct with the probes 110, 120. The outside air comes into contact with the heat conductive member 130.

The heat conductive member 130 has a function of equalizing the temperature of the skin surface where the probes 110, 120 are in contact with the living body 200, and the temperature of the surface where the probes 110, 120 are not in contact with the living body 200 and the peripheries thereof, that is, of creating an isothermal region. The formation of such an isothermal region establishes the desired thermal equivalent circuit as previously described.

A thickness of the heat conductive member 130 surrounding the probes 110, 120 need only be an optimal thickness for forming the isothermal region, taking into consideration the thermal resistance $R_A$ to the outside air, the thermal resistance R of the living body 200, and the like. More specifically, this thickness can be determined taking into consideration surface areas of the probes 110, 120 and the like, the area of the living body 200, blood flow, and the like.

Figure 7:
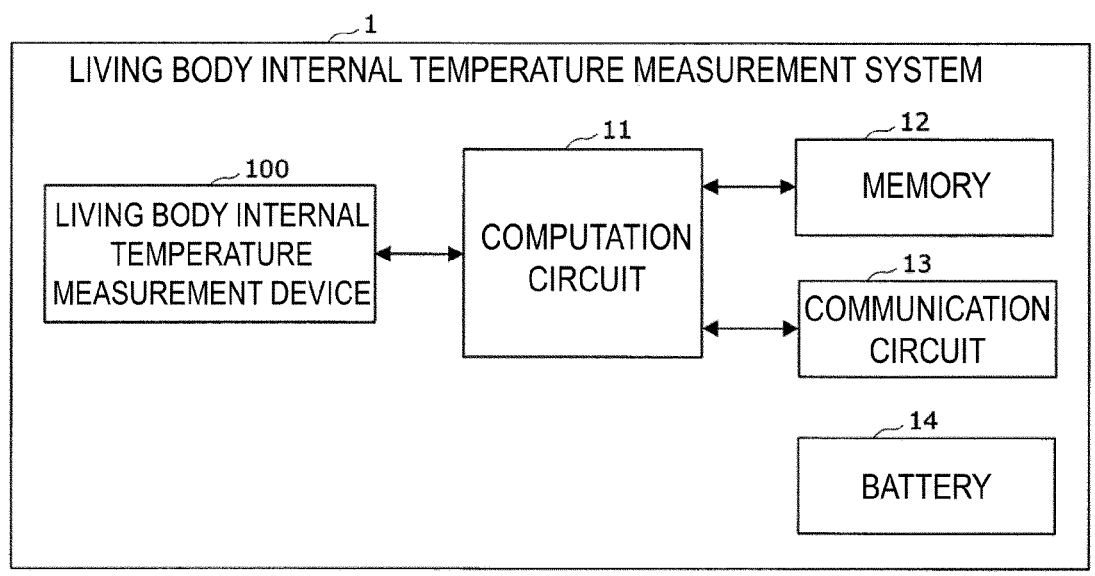
FIG. 7 is a block diagram illustrating a configuration example of a living body internal temperature measurement system including the living body internal temperature measurement device according to an embodiment of the present disclosure.
Figure 8:
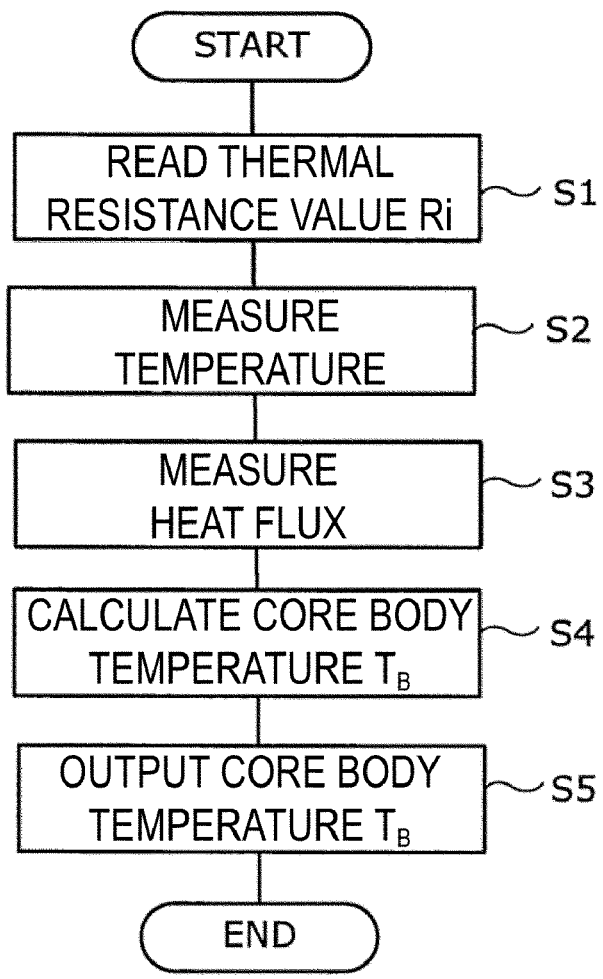
FIG. 8 is a flowchart for explaining an operation of the living body internal temperature measurement device according to an embodiment of the present disclosure.

FIG. 7 is a block diagram illustrating a configuration example of a living body internal temperature measurement system 1 including the living body internal temperature measurement device 100 having the configuration described above.

The living body internal temperature measurement system 1 includes the living body internal temperature measurement device 100, a computation circuit 11, a memory 12, a communication circuit 13 that functions as an interface (I/F) circuit with the outside, and a battery 14 that supplies power to the computation circuit 11, the communication circuit 13, and the like.

The computation circuit 11 estimates a core body temperature of the living body 200 on the basis of the heat fluxes measured by the heat flux sensors 112, 122 and the temperatures of the epidermis of the living body 200 measured by the temperature sensors 113, 123. More specifically, the computation circuit 11 estimates the core body temperature $T_B$ using equations (5) to (7) described above.

The computation circuit 11 generates and outputs time-series data of the estimated core body temperature $T_B$ of the living body 200. The time-series data are data in which the measurement time and the estimated core body temperature $T_B$ are associated with each other.

The memory 12 stores information related to an estimation model of the core body temperature $T_B$ (equations (5) to (7)) constructed in advance. In addition, the memory 12 stores the thermal resistance values of each of the probes 110, 120 in advance. The memory 12 can be realized by a predetermined storage region in a rewritable non-volatile storage device (flash memory, for example) provided in the living body internal temperature measurement system 1.

The communication circuit 13 outputs the time-series data of the core body temperature $T_B$ of the living body 200 generated by the computation circuit 11 to the outside. Such a communication circuit 13 is an output circuit to which a USB or other cable can be connected when outputting data or the like over a wire, but a wireless communication circuit in compliance with Bluetooth (trade name), for example, may be used.

Note that the living body internal temperature measurement system 1 includes a base member (not illustrated) having a sheet shape that functions as a base for placing the living body internal temperature measurement device 100, the computation circuit 11, the memory 12, the communication circuit 13, and the battery 14, and includes wiring (not illustrated) that electrically connects these elements.

Here, the living body internal temperature measurement system 1 is realized by a computer. Specifically, the computation circuit 11 is realized by a processor such as a central processing unit (CPU) or a digital signal processor (DSP), for example, executing various data processing in accordance with programs stored in storage devices such as a read-only memory (ROM), a random-access memory (RAM), and a flash memory including the memory 12 provided in the living body internal temperature measurement system 1. The programs described above for causing the computer to function as the living body internal temperature measurement system 1 can be recorded on a recording medium or provided through a network.

Temperature Measurement Method

A temperature measurement method executed by the temperature measurement device according to the present disclosure includes a first measurement step and a second measurement step. The first measurement step measures a physical quantity related to a temperature of a substance by the first probe on the basis of a first reference. The second measurement step measures a physical quantity related to a temperature of a substance by the second probe on the basis of a second reference different from the first reference.

Hereinafter, as a specific example of the temperature measurement method, a living body internal temperature measurement method executed by the living body internal temperature measurement device 100 is described with reference to the flowchart of FIG. 8. The living body internal temperature measurement device 100 is installed in advance in contact with the epidermis of the living body 200, and the following processes are executed.

First, the computation circuit 11 reads the thermal resistance value $R_i$ of each of the probes 110, 120 from the memory 12 (step S1). Next, each of the temperature sensors 113, 123 measures the temperature of the surface of the living body 200 (step S2). The measured temperatures are stored in the memory 12.

Next, each of the heat flux sensors 112, 122 measures the heat flux of the living body 200 (step S3). The measured heat flux values are stored in the memory 12. Subsequently, the computation circuit 11 reads the estimation model (equations (5) to (7)) of the core body temperature from the memory 12 and calculates the core body temperature $T_B$ (step S4).

More specifically, the core body temperature $T_B$ is estimated using a bridge circuit (first bridge circuit, second bridge circuit) that is formed in the thermal equivalent circuit, which includes the thermal resistance of the living body 200 and the thermal resistances of the probes 110, 120, and does not include the thermal resistance $R_A$ to outside air. The temperatures and heat fluxes of the surface of the living body 200 measured by the living body internal temperature measurement device 100 are input into the estimation model, and thus the core body temperature $T_B$ is estimated.

Subsequently, the calculated core body temperature $T_B$ is output from the communication circuit 13 (step S5). For example, the core body temperature $T_B$ can be transmitted to an external terminal via a communication network.

Here, the effect of the living body internal temperature measurement device 100 according to this embodiment will be described using FIG. 9. Note that, in the measurement illustrated in FIG. 9, aluminum was used as the heat conductive member 130. Furthermore, a thickness of 1 mm was used as the thickness of the aluminum on top surfaces of the probes 110, 120, and 5 mm was used as a thickness on side surfaces of the probes 110, 120.

Figure 9:
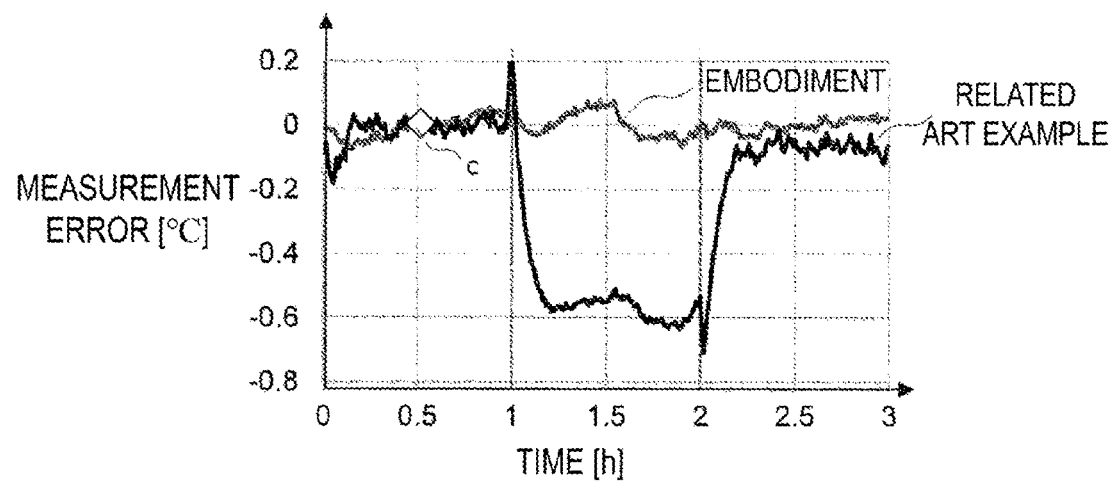
FIG. 9 is a diagram for explaining an effect of the living body internal temperature measurement device according to the embodiment.
Figure 10:
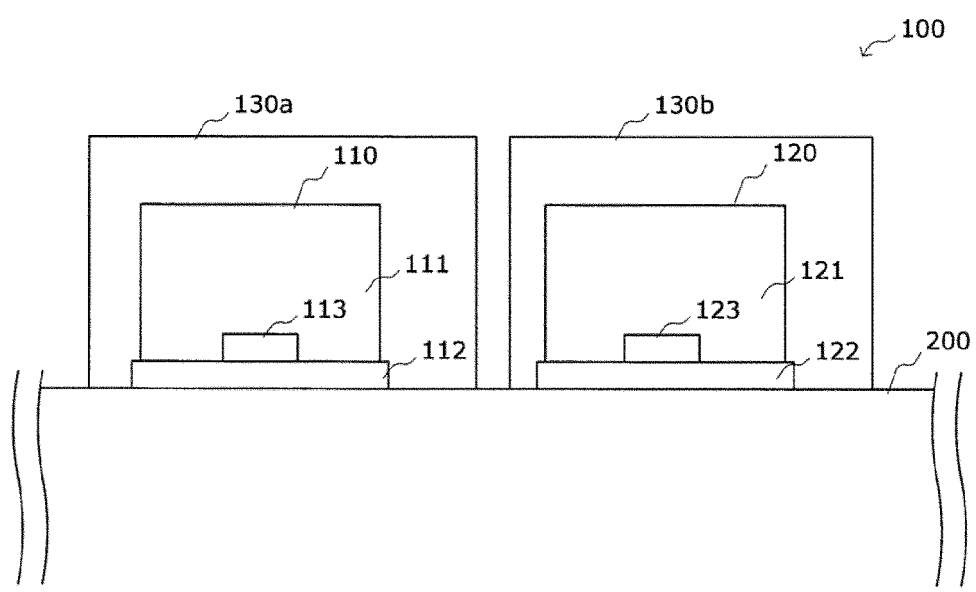
FIG. 10 is a block diagram illustrating a configuration of a living body internal temperature measurement device according to a first modification example.

FIG. 9 is a graph showing a measurement error in the core body temperature of a living body internal temperature measurement device according to a related art example that does not include the living body internal temperature measurement device 100 or the heat conductive member 130 of this embodiment. The horizontal axis represents time and the vertical axis represents the measurement error of the core body temperature. One hour from the start of measurement, the graph shows a measurement error of the measured core body temperature after calibration at point c inside a room. From one hour to two hours after the start of measurement, the graph shows a measurement error when the core body temperature was measured following calibration and movement to outside the room. Furthermore, from two hours to three hours after the start of measurement, the graph shows a measurement error when the core body temperature was measured following movement once again to inside the room.

As illustrated in FIG. 9, from the start of measurement to one hour, a room with no convection of outside air is assumed. In this period inside the room, after calibration is performed after the elapse of 0.5 hours from the start of measurement, the measurement error is slight in both this embodiment and the related art example. Subsequently, in the period from one hour to two hours after the start of measurement, when the core body temperature was estimated following movement to outside the room, the measurement error is approximately 0.1° C. in this embodiment, whereas the measurement error is significantly larger in the related art example due to the influence of the convection of the outside air.

Subsequently, in the period from two hours to three hours after the start of measurement, when the core body temperature was estimated following movement to inside the room once again, the measurement error remains a small value in this embodiment, whereas the measurement error of the related art example remains a large value compared to this embodiment.

Thus, it is understood that, in the living body internal temperature measurement device 100 according to this embodiment, even when the core body temperature is measured outside the room after calibration is performed inside the room, the measurement error is suppressed to an extremely small value.

As described above, according to the living body internal temperature measurement device 100 according to this embodiment, the surfaces on the outside air side of the probes 110, 120 disposed in contact with the epidermis of the living body 200 are covered by the heat conductive member 130 formed from a material having high thermal conductivity, such as a metal such as aluminum or copper or graphene.

Therefore, the estimation model does not include the thermal resistance $R_A$ to the outside air in the bridge circuit formed in the thermal equivalent circuit including the living body 200, the living body internal temperature measurement device 100, and the outside air, and the ratio K of the leakage of the heat fluxes does not depend on the thermal resistance $R_A$ to the outside air. Accordingly, in the living body internal temperature measurement device 100 according to this embodiment, even if the outside air changes, a measurement error can be suppressed and the core body temperature can be more accurately estimated.

First Modification Example

Next, a first modification example of the living body internal temperature measurement device 100 according to the embodiment described above will be described using FIG. 10. In the living body internal temperature measurement device 100 according to the embodiment, a case in which the heat conductive member 130 commonly covers the two probes 110, 120 has been described. In contrast, in the first modification example, heat conductive members 130a, 130b separately cover the peripheries of the probes 110, 120 disposed spaced apart from each other and in contact with the epidermis of the living body 200. Other configurations are the same as those of the embodiment described above.

In this way, the heat conductive member 130 is provided to each of the probes 110, 120, making it possible to reduce the size of the living body internal temperature measurement device 100.

Second Modification Example

Next, a second modification example of the living body internal temperature measurement device 100 according to the embodiment will be described using FIG. 11. In the embodiment and the first modification example described above, cases have been described in which the probes 110, 120 respectively include the heat flux sensors 112, 122 and the temperature sensor 113, 123. In contrast, the probes 110, 120 according to the second modification example respectively include a pair of temperature sensors 113a, 113b and a pair of temperature sensors 123a, 123b, in place of the heat flux sensors 112, 122.

Figure 11:
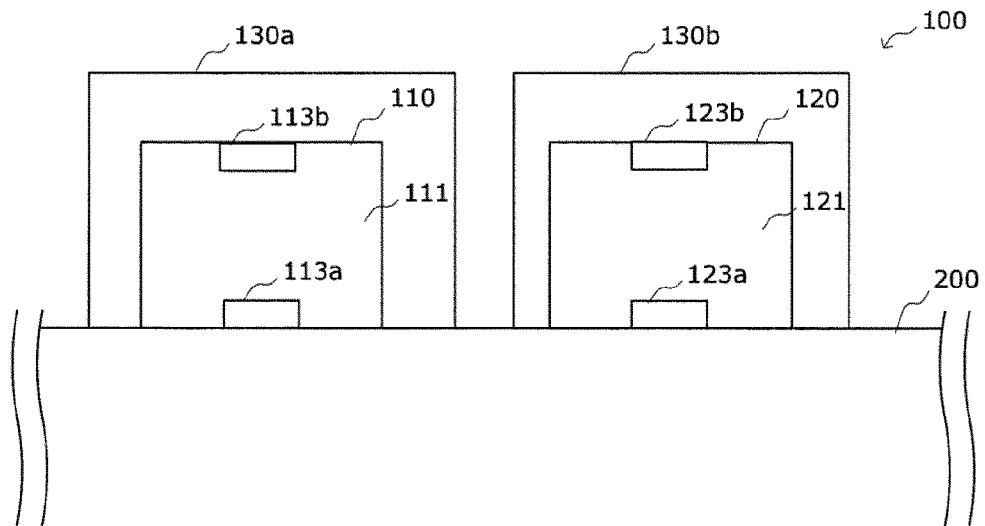
FIG. 11 is a block diagram illustrating a configuration of a living body internal temperature measurement device according to a second modification example.

In the second modification example illustrated in FIG. 11, the heat conductive members 130a, 130b are respectively provided to the probes 110, 120, similar to the first modification example described above.

The temperature sensor 1130a is disposed in contact with the epidermis at the end portion of the heat insulating member 111 of the probe 110 on the epidermis side of the living body 200. Further, the other temperature sensor 113b is provided on the other end of the heat insulating member 111 at a position away from the epidermis of the living body 200. The temperature sensor 130a on the epidermis side measures the temperature of the epidermis of the living body (hereinafter, also referred to as temperature $T_1$). The temperature sensor 113b measures the temperature of the epidermis of the living body 200 via the heat insulating member 111 (hereinafter also referred to as temperature $T_3$).

A heat flux $H_1$ (corresponding to $H_i$ in FIGS. 1 and 2) in the probe 110 is derived from a temperature difference measured by the temperature sensors 113a, 113b ($H_1=(T_1-T_3)$).

Note that, for the other probe 120 as well, the heat flux in the probe 120 can be found from the difference in the temperatures measured by the temperature sensors 123a and 123b.

In this way, even when the temperature and the heat flux of the epidermis of the living body 200 are measured using the two temperature sensors 113a, 113b and 123a, 123b instead of the heat flux sensors 112, 122, it is possible to more accurately estimate the core body temperature regardless of changes in the outside air, similar to the embodiment described above.

Third Modification Example

Next, a third modification example according to the embodiment will be described using FIG. 3. In the second modification example described above, a case has been described in which the pairs of temperature sensors 113a, 113b, and 123a, 123b, are respectively provided at both ends of the heat insulating members 111, 121 instead of the heat flux sensors 112, 122 to calculate the temperatures and heat fluxes of the epidermis of the living body 200. Further, in the second modification example, a case has been described in which the heat conductive members 130a, 130b separately and respectively cover the peripheries of the probes 110, 120 on the outside air side, the probes 110, 120 being disposed on the surface of the living body 200 apart from each other.

Figure 12:
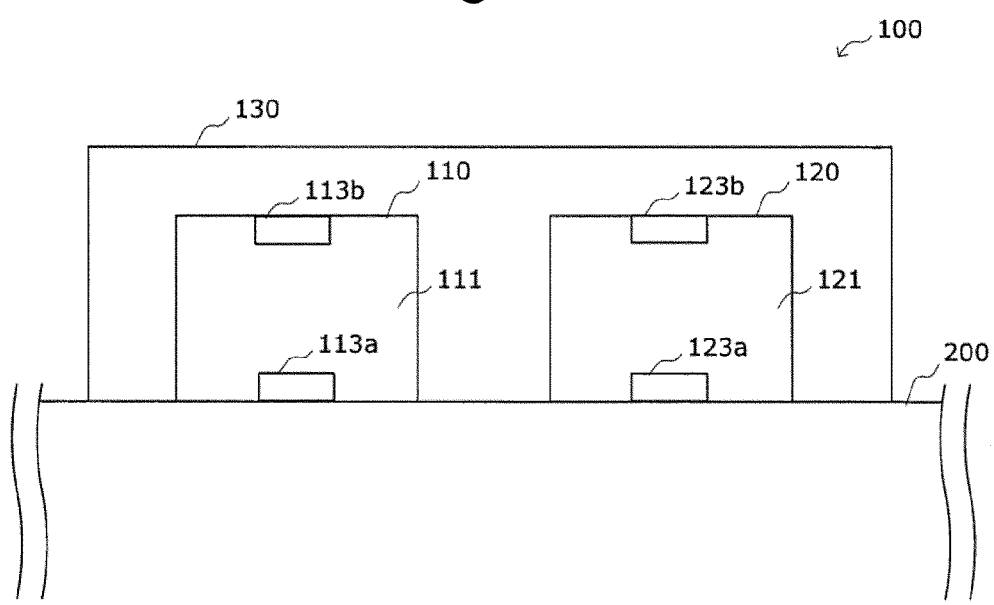
FIG. 12 is a block diagram illustrating a configuration of a living body internal temperature measurement device according to a third modification example.

On the other hand, in the third modification example, as illustrated in FIG. 12, there is provided the heat conductive member 130 that commonly covers, other than the surfaces in contact with the surface of the living body 200, the peripheries of the probes 110, 120, respectively provided with the two temperature sensors 113a, 113b, and 123a, 123b, at both ends of the heat insulating members 111, 121, the temperature sensors 113a, 113b and 123a, 123b, having the same configuration as that in the second modification example.

In this way, the heat conductive member 130 having a high thermal conductivity and formed from a metal material or a graphene sheet covers the peripheries of the two probes 110, 120, and thus a configuration supported by the estimation model (equations (5) and (7)) of the core body temperature described above can be used.

Fourth Modification Example

Next, a fourth modification example of the living body internal temperature measurement device 100 according to the embodiment will be described using FIG. 13. In the second modification example and the third modification example, cases have been described in which the two temperature sensors 113a, 113b, and 123a, 123b, are respectively provided at both ends of the heat insulating members 111, 121 for each of the probes 110, 120. In contrast, in the fourth modification example, the probes 110, 120 respectively include the temperature sensors 113, 123 that come into contact with the epidermis of the living body 200, but a temperature sensor 140 is provided in an interior of the heat conductive member 130.

Figure 13:
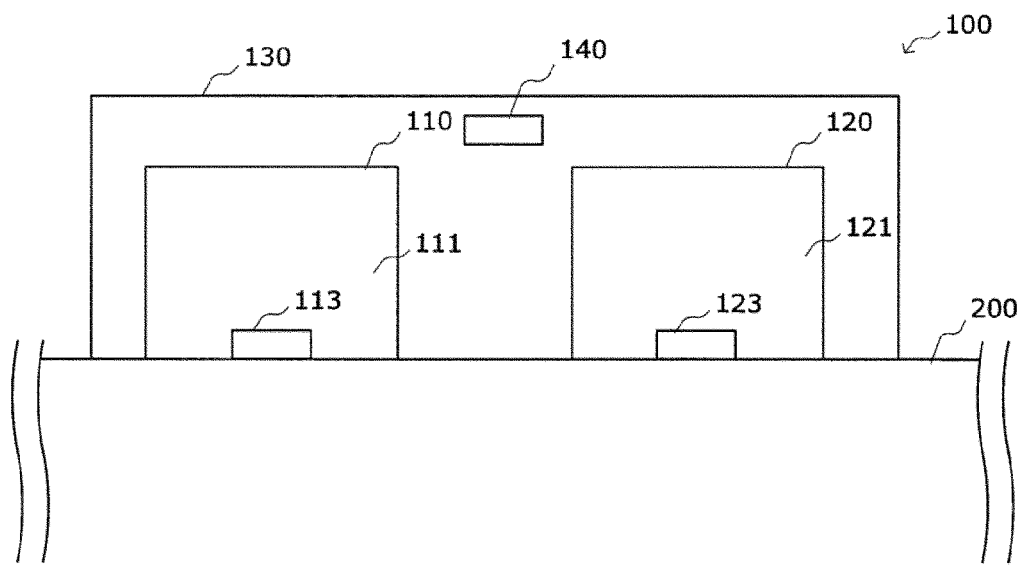
FIG. 13 is a block diagram illustrating a configuration of a living body internal temperature measurement device according to a fourth modification example.
Figure 14:
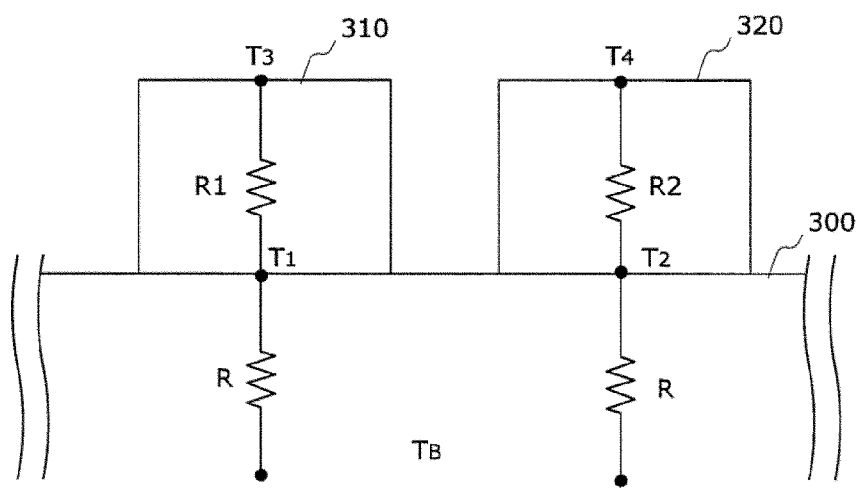
FIG. 14 is a block diagram illustrating a configuration of a living body internal temperature measurement device in a related art.
Figure 15:
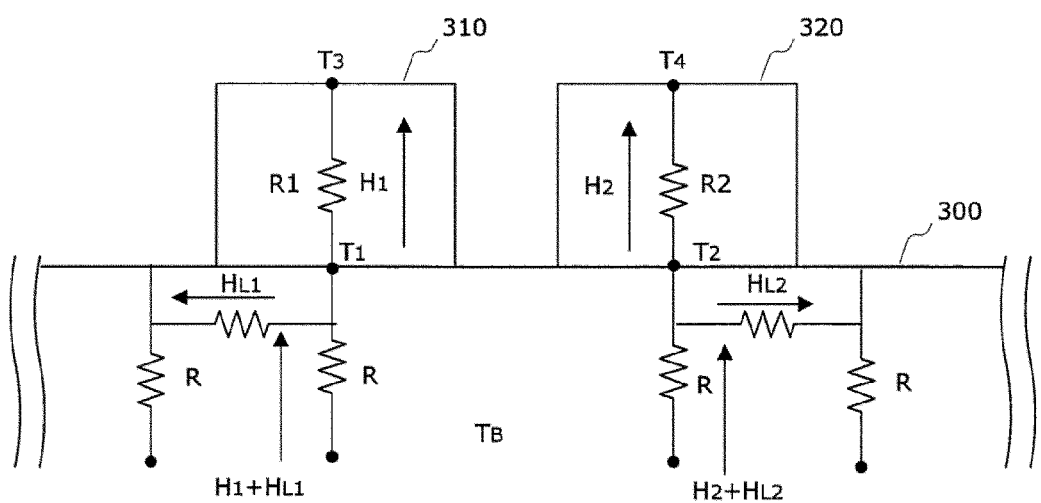
FIG. 15 is a block diagram illustrating a configuration of the living body internal temperature measurement device in the related art.

As illustrated in FIG. 13, in the fourth modification example, the temperature sensors described in the third modification example are not provided to the other ends of the heat insulating member 111, 121 away from the living body 200. Instead, the temperature sensor 140, which is commonly used in the two probes 110, 120, is provided covered by the heat conductive member 130. Thus, the living body internal temperature measurement device 100 measures the temperature and the heat flux of the surface of the living body 200 using a total of three temperature sensors.

The temperature of the living body 200 measured by the temperature sensor 140 is measured as the temperature $T_3$ described in the second modification example and the third modification example described above, and the heat fluxes of the probes 110, 120 are respectively derived from the differences between the temperature $T_3$ and the temperatures measured by the temperature sensors 113, 123.

In this way, in the fourth modification example, the number of temperature sensors provided in the living body internal temperature measurement device 100 need only be three, and thus a simpler sensor configuration can be achieved.

Although the embodiments of the living body internal temperature measurement device and the living body internal temperature measurement method of the present disclosure have been described above, the present disclosure is not limited to the described embodiments, and various types of modification that can be conceived by a person skilled in the art can be made within the scope of the disclosure described in the aspects.

REFERENCE SIGNS LIST

1 Living body internal temperature measurement system
100 Living body internal temperature measurement device
110, 120 Probe
130 Heat conductive member
111, 121 Heat insulating member
112, 122 Heat flux sensor
113, 123 Temperature sensor
200 Living body
11 Computation circuit
12 Memory
13 Communication circuit
14 Battery.

The invention claimed is:

1. A temperature measurement device comprising:
   a first probe configured to measure a physical quantity related to a first temperature of a substance based on a first reference, wherein the first probe is configured to physically contact the substance;
   a second probe configured to measure a physical quantity related to a second temperature of the substance based on a second reference different from the first reference, wherein the second probe is configured to physically contact the substance; and
   a heat conductive member covers the first probe and the second probe, wherein the heat conductive member physically contacts and extends continuously from a sidewall of the first probe to a sidewall of the second probe, and wherein the heat conductive member is configured to thermally conduct heat from the substance.

2. The temperature measurement device according to claim 1, wherein:
   the first probe comes into contact with a surface of a living body to measure a physical quantity related to a first temperature of the living body,
   the second probe has a thermal resistance different from a thermal resistance of the first probe and comes into contact with the surface of the living body to measure a physical quantity related to a second temperature of the living body, and
   the heat conductive member thermally conducts heat transferred from the surface of the living body.

3. The temperature measurement device according to claim 1, wherein the heat conductive member comprises a material having a thermal conductivity higher than a thermal conductivity of air.

4. The temperature measurement device according to claim 3, wherein the heat conductive member comprises a metal material.

5. The temperature measurement device according to claim 4, wherein the heat conductive member comprises aluminum or copper.

6. The temperature measurement device according to claim 3, wherein the heat conductive member comprises graphene.

7. The temperature measurement device according to claim 1, wherein:
   the first probe comprises:
      a first thermal resistor;
      a first temperature measurement device connected to the first thermal resistor and configured to measure the first temperature of the substance; and
      a first heat flux measurement device connected to the first thermal resistor and configured to measure a first heat flux; and
   the second probe includes:
      a second thermal resistor having a thermal resistance different from a thermal resistance of the first thermal resistor;
      a second temperature measurement device connected to the second thermal resistor and configured to measure the second temperature of the substance; and
      a second heat flux measurement device connected to the second thermal resistor and configured to measure a second heat flux.

8. A temperature measurement method comprising:
   calculating, using a first bridge circuit including a thermal resistance of a substance and a thermal resistance of a first probe, a first temperature of a substance physically contacting and measured by the first probe;
   calculating, using a second bridge circuit including the thermal resistance of the substance and a thermal resistance of a second probe, a second temperature of the substance physically contacting and measured by the second probe, wherein a heat conductive member covers the first probe and the second probe, wherein the heat conductive member physically contacts and extends continuously from a sidewall of the first probe to a sidewall of the second probe, and wherein the heat conductive member is configured to thermally conduct heat from the substance; and
   estimating a temperature of a deep area of the substance based on the first temperature and the second temperature.

9. The temperature measurement method according to claim 8, wherein the thermal resistance of the second probe is different from a thermal resistance of the first probe.

10. The temperature measurement method according to claim 9, further comprising:
    contacting, with the first probe, a surface of a living body to measure a physical quantity related to the first temperature, wherein the first temperature is of the living body;
    contacting, with the second probe, the surface of the living body to measure a physical quantity related to the second temperature, wherein the second temperature is of the living body; and
    the heat conductive member thermally conducts heat transferred from the surface of the living body.

11. The temperature measurement method according to claim 8, wherein the heat conductive member comprises a material having a thermal conductivity higher than a thermal conductivity of air.

12. The temperature measurement method according to claim 11, wherein the heat conductive member comprises a metal material.

13. The temperature measurement method according to claim 12, wherein the heat conductive member comprises aluminum or copper.

14. The temperature measurement method according to claim 11, wherein the heat conductive member comprises graphene.

* * * * *